United States Patent
Muñoz De Diego et al.

(10) Patent No.: US 8,519,167 B2
(45) Date of Patent: Aug. 27, 2013

(54) METHOD FOR THE PREPARATION OF 2,5-FURANDICARBOXYLIC ACID AND ESTERS THEREOF

(75) Inventors: Cesar Muñoz De Diego, Amsterdam (NL); Wayne Paul Schammel, San Francisco, CA (US); Matheus Adrianus Dam, Amsterdam (NL); Gerardus Johannes Maria Gruter, Amsterdam (NL)

(73) Assignee: Furanix Technologies B.V., Amsterdam (NL)

( * ) Notice: Subject to any disclaimer, the term of this patent is extended or adjusted under 35 U.S.C. 154(b) by 0 days.

(21) Appl. No.: 13/497,682

(22) PCT Filed: Oct. 6, 2010

(86) PCT No.: PCT/NL2010/050653
§ 371 (c)(1),
(2), (4) Date: Jul. 11, 2012

(87) PCT Pub. No.: WO2011/043660
PCT Pub. Date: Apr. 14, 2011

(65) Prior Publication Data
US 2012/0283452 A1    Nov. 8, 2012

Related U.S. Application Data

(60) Provisional application No. 61/249,400, filed on Oct. 7, 2009.

(30) Foreign Application Priority Data

Oct. 7, 2009  (NL) ...................................... 2003607

(51) Int. Cl.
*C07D 307/68*  (2006.01)

(52) U.S. Cl.
USPC ....................................................... 549/485

(58) Field of Classification Search
USPC ......................................................... 549/485
See application file for complete search history.

(56) References Cited

U.S. PATENT DOCUMENTS

| 2,628,249 A | 2/1953 | Bruno, Jr. |
| 3,173,933 A | 3/1965 | Hay |
| 4,977,283 A | 12/1990 | Leupold et al. |
| 2012/0059178 A1* | 3/2012 | Sanborn ........................ 549/485 |

FOREIGN PATENT DOCUMENTS

| GB | 621971 | 10/1947 |
| WO | 01/72732 A2 | 10/2001 |
| WO | 2007/104514 A2 | 9/2007 |
| WO | 2009/030509 A2 | 3/2009 |

OTHER PUBLICATIONS

W. Partenheimer, "Methodology and scope of metal/bromide autoxidation of hydrocarbons", Catalysis Today 23 (1995), pp. 69-158.

Walt Partenheimer et al., "Synthesis of 2,5-Diformylfuran and Furan-2,5-Dicarboxylic Acid by Catalytic Air-Oxidation of 5-Hydroxymethylfurfural. Unexpectedly Selective Aerobic Oxidation of Benzyl Alcohol to Benzaldehyde with Metal/Bromide Catalysts" Adv. Synth. Catal., 343, No. 1, Jan. 1, 2001, p. 102-111.

Taarning et al., "Chemicals from Renewables: Aerobic Oxidation of Furfural and Hydroxymethylfurfural over Gold Catalysts" ChemSusChem 2008 1, 1-5.

* cited by examiner

*Primary Examiner* — Kristin Vajda
(74) *Attorney, Agent, or Firm* — Hoffmann & Baron, LLP

(57) ABSTRACT

A method for the preparation of 2,5-furandicarboxylic acid ("FDCA") and/or an alkyl ester of FDCA includes the step of contacting a feed comprising a starting material selected from 5-alkoxymethylfurfural, 2,5-di(alkoxymethyl)furan and a mixture thereof with an oxidant in the presence of an oxidation catalyst. The feed may also comprise 5-hydroxymethylfurfural as a further starting material.

17 Claims, No Drawings

METHOD FOR THE PREPARATION OF 2,5-FURANDICARBOXYLIC ACID AND ESTERS THEREOF

CROSS-REFERENCE TO RELATED APPLICATIONS

This application is the National Stage of International Application No. PCT/NL2010/050653, filed Oct. 6, 2010, which claims the benefit of Netherlands Application No. 2003607, filed Oct. 7, 2009, and U.S. Provisional Application No. 61/249,400, filed Oct. 7, 2009, the contents of all of which are incorporated by reference herein.

FIELD OF THE INVENTION

The present invention relates to a method for the preparation of 2,5-furandicarboxylic acid and esters thereof, in particular 2,5-furandicarboxylic acid ("FDCA) and/or alkyl esters of FDCA from alkyl ethers of 5-hydroxymethylfurfural ("HMF"), also known as 5-(alkoxymethyl)-2-furaldehyde, from 2,5-bis(alkoxymethyl)furan or from a mixture thereof. Mixtures of one or more of these starting materials with HMF may also be used.

BACKGROUND OF THE INVENTION 2,5-Furandicarboxylic acid is a furan derivative. This organic compound was first obtained by Fittig and Heinzelmann in 1876. The first review, by Henry Hill was published in 1901 (Am. Chem. Journ. 25, 439). FDCA was more than 125 years later identified by the US Department of Energy as one of 12 priority chemicals for establishing the "green" chemistry industry of the future. However, to date, no commercial process exists for its production. On the laboratory scale it is often synthesized from HMF, which in turn can be obtained from carbohydrate-containing sources such as glucose, fructose, sucrose and starch. From fructose and glucose HMF is obtained by acidic elimination of three moles of water.

The derivatives of HMF are identified as potential and versatile fuel components and precursors for the production of plastics. The polyester from 2,5-furandicarboxylic acid dimethyl ester and ethylene glycol was first reported in 1946 (GB 621,971).

WO 01/72732 describes the oxidation of HMF to FDCA. The maximum FDCA yield reported is 59%, obtained at 105° C. The oxidation of HMF in an aqueous medium with oxygen using a catalyst from the Pt-group is described in U.S. Pat. No. 4,977,283. Taarning et al. described the oxidation of HMF over gold based catalysts (ChemSusChem, 1, (2008), 75-784).

Partenheimer et al describe the synthesis of furan-2,5-dicarboxylic acid by catalytic air-oxidation of 5-hydroxymethylfurfural with the metal/bromide catalyst Co/Mn/Br in Adv. Synth. Catal. 2001, 343, pp 102-11.

In WO 2007/104514, the synthesis of ethers of HMF such as 5-methoxymethylfurfural (MMF) and 5-ethoxymethylfurfural (EMF) from biomass sources is described. Given the higher stability than HMF and hence improved production pathways and given the green reputation of these ethers, they were considered by the present inventors as interesting starting point in the preparation of furan-based monomers that could be used for the production of furandicarboxylic acid-based polyesters, for instance as an alternative for PET or FDCA-based polyamids (nylons). One of the most important conventional, oil-based, polyester monomers is Purified Terephthalic Acid (PTA) and their alkyl esters such as DiMethyl Terephthalate (DMT). The di-esters are of interest in the polymerization process, as methanol is liberated as condensation product in the reaction of DMT with a diol instead of higher boiling water that is liberated in the reaction of PTA with a diol. The lower boiling point of methanol facilitates the required removal during the polycondensation step, facilitating the formation of high molecular weight polymers.

Oxidation of the HMF ethers has not been reported. When using prior art techniques such as the above described catalyst systems, the desired FDCA could be obtained in moderate yield. Surprisingly, it was found that when using a bromide-containing cobalt and manganese-based catalyst, under specific reaction conditions, not only FDCA was obtained but that also significant amounts of esters could be obtained from direct oxidation of the ether function of HMF ethers. The FDCA+FDCA ester combined yields are with 70-85% very high. From a process point of view this is very interesting. Thus for 5-(methoxymethyl)furfural or MMF the formation of the mono methyl ester of FDCA was observed.

SUMMARY OF THE INVENTION

In conclusion, the present inventors have now found that HMF alkyl ethers or 2,5-bis(alkoxymethyl)furan can be oxidized to FDCA and alkyl esters thereof. Thus, in a first aspect the invention provides a method for the preparation of 2,5-furandicarboxylic acid or an alkyl ester of 2,5-furandicarboxylic acid comprising the step of contacting a feed comprising a starting material selected from 5-alkoxymethyl furfural, 2,5-bis(alkoxymethyl)furan and a mixture thereof with an oxidant in the presence of an oxidation catalyst. Optionally, the feed may also comprise HMF as a further starting material. As an example, the oxidation catalyst preferably comprises at least one metal selected from cobalt and manganese, more preferably both, and suitably further comprises a source of bromine, preferably a bromide.

DETAILED DESCRIPTION OF THE INVENTION

5-Alkoxymethyl furfural can be obtained from biomass sources as described in WO 2007/104514. Depending on the process conditions the product obtained in accordance with the process of this reference may also contain HMF. 2,5-Bis (alkoxymethyl)furan, can be produced from HMF and from 5-alkoxymethyl furfural as described in WO 2009/030509.

The product of the reaction of the current invention with 5-(alkoxymethyl)furfural can be FDCA, or a mixture of FDCA and the monoalkylester (hemi-ester) of FDCA, depending on the process conditions and the catalyst selection and concentration. For example, when a Co/Mn/Br based catalyst is used, the Co/Mn/Br stoichiometry and concentration of the catalyst has a significant impact. Likewise, when the feed comprises 2,5-bis(alkoxymethyl)furan, the product of the reaction can be FDCA, a mixture of FDCA and the monoalkylester (hemi-ester) of FDCA, or a mixture of FDCA, the monoalkylester (hemi-ester) of FDCA and the dialkyl ester of FDCA, again depending on the process conditions and the catalyst selection and concentration.

The alkyl group in 5-(alkoxymethyl)furfural or in 2,5-bis (alkoxymethyl)furan can suitably be $C_1$-$C_5$ alkyl, i.e. methyl, ethyl, propyl, isopropyl, butyl, 2-butyl, tert-butyl, pentyl, 2-pentyl, neopentyl or 3-pentyl. There is a preference for methyl, and to a lesser extent, also ethyl, as explained hereafter. For HMF, 5-(methoxymethyl)furfural and 5-(ethoxymethyl)furfural, the products contain FDCA (R=H), FDCA and the monomethylester (hemi-ester) of FDCA (R=Me), or FDCA and the monoethylester (hemi-ester) of FDCA (R=Et), respectively.

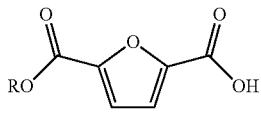

R = H, Me or Et

The product of the reaction can be used in the preparation of a polyester, by reaction thereof with a suitable diol. Such polyester preparations are preferably performed by transesterification, whereby the di-methyl ester or di-ethyl ester of FDCA is used and wherein the methyl or ethyl groups are exchanged in the form of a volatile alcohol during the transesterification with the diol. Accordingly, there is a preference for methyl, and to a lesser extent, also ethyl as alkyl group.

In case a bromine containing catalyst is used, the bromine source can be any compound that produces bromide ions in the reaction mixture. These compounds include hydrogen bromide, sodium bromide, elemental bromine, benzyl bromide, tetrabromoethane. Also other bromine salts, such as an alkali or earth alkali metal bromine or another metal bromide such as $ZnBr_2$ can be used. There is a preference for hydrobromic acid or sodium bromide. The amount of bromine mentioned in here relates to the amount measured as Br relative to cobalt. The oxidation catalyst, as mentioned above, preferably comprises at least one metal selected from the group consisting of Co and Mn, preferably both.

In the processes according to the current invention that make use of cobalt, manganese and bromide catalyst, a cobalt compound and a manganese compound and a bromine-containing compound are used. These compounds are preferably soluble in the reaction mixture.

The bromide catalyst that also contains Co and Mn can optionally contain one or more additional metals, in particular Zr and/or Ce. Alternative and suitable catalysts are described in W. Partenheimer, Catalysis Today 23(2), 69-158 (1995) in particular on pages 89-99, included herein by reference.

Each of the metal components can be provided in any of their known ionic forms. Preferably the metal or metals are in a form that is soluble in the reaction solvent. Examples of suitable counterions for cobalt and manganese include, but are not limited to, carbonate, acetate, acetate tetrahydrate and halide, with bromide being the preferred halide.

As described in Partenheimer, ibid, pages 86-88, suitable solvents for use in the processes of the present invention, described above, preferably have at least one component that contains a monocarboxylic acid functional group. The solvent may also function as one of the reagents. The processes may be run in a solvent or solvent mixture that does not contain an acid group. In that case, preferably one of the reagents does contain a monocarboxylic acid functional group. Suitable solvents can also be aromatic acids such as benzoic acid and derivatives thereof. A preferred solvent is an aliphatic $C_2$-$C_6$ monocarboxylic acid, such as but not limited to acetic acid, propionic acid, n-butyric acid, isobutyric acid, n-valeric acid, trimethylacetic acid, and caproic acid and mixtures thereof. Said mixtures may also include benzene, acetonitrile, heptane, acetic anhydride, chlorobenzene, o-dichlorobenzene, and water. Most preferred as solvent is acetic acid ("AcOH").

The oxidant in the processes of the present invention is preferably an oxygen-containing gas or gas mixture, such as, but not limited to air and oxygen-enriched air. Oxygen by itself is also a preferred oxidant.

The processes of the instant invention described above can be conducted in a batch, semi-continuous or continuous mode. Especially for the manufacture of FDCA, operation in the batch mode with increasing temperature at specific times, increasing pressure at specific times, variation of the catalyst concentration at the beginning of the reaction, and variation of the catalyst composition during the reaction is desirable. For example, variation of the catalyst composition during reaction can be accomplished by addition of cobalt and/or manganese and/or zirconium, and/or cerium, and/or bromide at specified times.

The temperature and pressure in a commercial process can be selected from wide ranges. When the reaction is conducted in the presence of a solvent the reaction temperature and pressure are not independent. The pressure is determined by the solvent (e.g., acetic acid) pressure at a certain temperature. The pressure of the reaction mixture is preferably selected such that the solvent is mainly in the liquid phase. In practice this means that pressures between 5 and 100 bar can be used with a preference for pressures between 10 and 80 bars, depending on the desired product (diacid or (hemi) ester). In case the oxidant is an oxygen-containing gas, such as air, the gas can be continuously fed to and removed from the reactor, or the gas can be supplied all at the start of the reaction. In the latter case, the pressure of the system will depend on the headspace volume and the amount of gas required to convert the starting material. It is clear that in the latter case, the pressure of the system may be significantly higher than when an oxygen containing gas is continuously fed and removed.

The temperature of the reaction mixture is suitably between 60 and 220° C., preferably between 100 and 210° C., more preferably between 150 and 200° C., most preferably between 160 and 190° C. Temperatures higher than 180° C. tend to lead to decarboxylation and to other degradation products. Good results (FDCA+FDCA esters) have been achieved at a temperature of about 180° C.

In the preferred oxidation catalysts, molar ratios of cobalt to manganese (Co/Mn) are typically 1/1000-100/1, preferably 1/100-10/1 and more preferably 1/10-4/1.

Likewise, in the preferred oxidation catalysts, molar ratios of bromine to metals (e.g. Br/(Co+Mn)) are typically from 0.001 to 5.00, preferably 0.01 to 2.00 and more preferably 0.1 to 0.9.

Catalyst concentration (calculated on the metal, e.g., Co+Mn) is preferably between 0.1 and 10 mol % relative to the starting material, with a preference for loads between 2 and 6 mol %. Good results were obtained in general with catalyst loads of around 4 mol %.

In another aspect, the monoester of the present invention or the mixture of FDCA and mono- and/or diester of FDCA can be transformed using common esterification reactions to a diester by contacting the starting material(s) under appropriate conditions with the relevant alcohol. Thus, in one aspect, the invention also relates to the use of the monoalkylester of 2,5-furandicarboxylic acid or the mixture of FDCA and mono- and/or diester of FDCA in the preparation of a dialkylester of 2,5-dicarboxylic acid by reaction of the monomethylester of 2,5-furandicarboxylic acid or the mixture of FDCA and mono- and/or diester of FDCA with a $C_1$-$C_5$ alkyl alcohol, preferably the alcohol required to prepare the symmetric alkylester of 2,5-furandicarboxylic acid (i.e. both alkyl groups are identical) and more preferably to the use of the monomethylester of 2,5-furandicarboxylic acid or the mixture of FDCA and mono- and/or dimethyl ester of FDCA in the preparation of a dimethyl ester of FDCA.

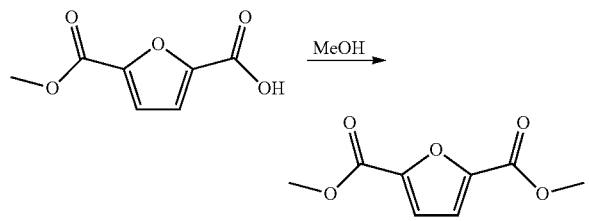

Accordingly, the present invention also provides a method for the preparation of a dialkylester of 2,5-furandicarboxylic acid, comprising preparing 2,5-furandicarboxylic acid or an alkyl ester of 2,5-furandicarboxylic acid in a method as described above to obtain a reaction product, and reacting the reaction product with a $C_1$-$C_5$ alkyl alcohol to obtain the dialkyl ester of 2,5-furandicarboxylic acid. The alkyl group in the latter $C_1$-$C_5$ alkyl alcohol is preferably the same as the alkyl group in the starting material so that a symmetrical dialkyl ester of 2,5-furandicarboxylic acid is obtained. The alkyl groups are preferably methyl groups. The reaction may be performed as described in U.S. Pat. No. 2,628,249, in the presence of sulphuric acid or a sulphonic acid, with optionally activated carbon being present as well.

In a further aspect of the invention, the esters of the invention and in particular the di-methylester can be used in the preparation of polyester polymers by reaction with a diol. Reacting the di-methylester with a diol will result in the formation of methanol that quickly vaporises. In 1946 the polymerization of FDCA dimethyl ester with ethylene glycol was described as a first example of such a polymerization in GB 621,971.

The starting materials for the production of FDCA may originate from a carbohydrate source as described above. Examples of such disclosures are WO 2007/104515 and WO 2009/030509. Accordingly, the invention also provides a method for the preparation of 2,5-furandicarboxylic acid and an alkyl ester of 2,5-furandicarboxylic acid, wherein a carbohydrate source is converted into products comprising 5-alkoxymethyl furfural and optionally 5-hydroxymethyl furfural, from which is isolated a feed comprising 5-alkoxymethyl furfural and optionally 5-hydroxymethyl furfural, and which method further comprises the subsequent step of contacting the feed with an oxidant in the presence of an oxidation catalyst, in particular a cobalt and manganese and bromide-containing catalyst, under appropriate reaction conditions. The subsequent step is preferably carried out in a method as described above.

Indeed, polyesters are generally made by a combined esterification/polycondensation reaction between monomer units of a diol (e.g., ethylene glycol (EG)) and a dicarboxylic acid. Additives such as catalysts and stabilizers may be added to facilitate the process and stabilize the polyester towards degradation.

EXAMPLES

Experiments were carried out in parallel 12 ml magnetically stirred stainless steel batch reactors. The reactors are grouped in blocks containing 12 batch reactors. The standard procedure for all the reactions was as follows: 0.5 ml of feed stock solution in acetic acid (1.56 M) were added into a reactor lined with a Teflon insert. 1 ml of a catalyst stock solution in acetic acid was subsequently added to the reactor. In a typical experiment, a catalyst composition Co/Mn/Br with a relative 1-x-y ratio, the concentration of Co (OAc)$_2$ *4H$_2$O was 0.78 mg/ml (0.31 mmol/ml). As a Mn source, Mn(OAc)$_2$*4H$_2$O was used and as a bromine source NaBr was used. The reactors were closed with a rubber septum, after which the reactors were sealed and pressurized to the desired air pressure, ranging from 20-60 bars. After pressurization, the block with 12 reactors was placed in the test unit which was preheated at the desired temperature, ranging from 100 to 220° C. After the desired reaction time, ranging from 0.5 hr to 24 hrs, the block is placed into an ice bath for 20 minutes. When the block had cooled down, it was depressurized. After opening, HPLC samples were prepared. First 5 ml of a saccharine solution in DMSO (11.04 mg/ml) was added to the each reactor and the mixture was stirred for 5 minutes. Then 10 μl of this mixture was diluted to 1000 μl with water in a HPLC vial. The samples were analyzed using HPLC.

Example 1

Example 1 shows the combined yield ("y") of FDCA+ FDCA mono-alkyl ester in the oxidation of EMF, MMF, a 1:1 mixture of HMF+EMF and a 1:1 mixture of HMF+MMF, respectively with 0.78 mol % Co catalyst (relative to the feed), 0.52 M feed concentration and Co/Mn/Br ratios of 1/5/5, 1/5/20 and 1/3/20 at 180° C. for 1 hr with 60 bar air. The oxygen to feed ratio was 8.07 mol of O$_2$ per mole feed. Under these conditions, higher Br amounts give higher yields but when Br/(Co+Mn)>1, corrosion may become a problem on commercial scale. Surprisingly, MMF gives slightly higher yields than EMF.

Example 1 further shows the selectivity ("s") to FDCA and to FDCA monoalkyl ester (FDCA1/2R) for the EMF and MMF oxidations. Under these conditions, MMF showed higher ester selectivities than EMF and the lower bromine amounts show higher ester selectivities. The data of these experiments are given in Table 1.

It is surprising that the oxidations of EMF and MMF are also complete after 1 hour, and provide almost the same yield on furandicarboxylics as HMF. This is contrary to the teachings of the prior art that indicates that a significantly lower amount of products may be expected in the oxidation of an ether. In U.S. Pat. No. 3,173,933 the oxidation of alcohols and ethers over a cobalt and bromine-containing catalyst has been described. It appeared that the yield of oxidation products such as a carboxylic acid and the corresponding ester is significantly higher when an alcohol is oxidised compared to the oxidation of an ether.

Example 2

Example 2 shows the effect of absolute catalyst amounts on the combined yield of FDCA+FDCA mono-methyl ester in the oxidation of MMF with 0.1, 0.78, 1.56 and 1.85 mol % Co catalyst (relative to the feed), 3.7 wt/wt % feed concentration and Co/Mn/Br ratios of 1/5/5, 1/3/20 and 1/5/20 at 180° C. for 1 hr with 60 bar air. The oxygen to feed ratio was 8.07 mol of O$_2$ per mole feed. Under these conditions, the lowest catalyst concentration (0.1 mol % Co) gives 25-45% yields of FDCA+ FDCA methyl ester. With 0.78 mol % Co, the low bromine catalyst system (1/5/5) gives a 60% yield of FDCA+FDCA methyl ester, while the higher Br catalysts (1/3/20 and 1/5/20) give 70-80% yields of FDCA+FDCA methyl ester. Higher catalyst concentrations (1.56 mol % and 1.95 mol %) give FDCA+FDCA methyl ester yields of 70-80%, independent of Mn or Br amount (within the range tested).

Example 2 further shows the selectivity to FDCA monomethyl ester (FDCA1/2R) for MMF oxidations. Under these conditions, the low Br catalyst (1/5/5) showed higher ester selectivities than the higher Br catalysts (1/3/20 and 1/5/20). The Co/Mn ratio's 1/5 and 1/3 give identical results. The 0.78 mol % Co catalyst system gives the highest ester yields. The data of these experiments are given in Table 2.

Example 3

Example 3 shows the effect of air pressure (20, 40 and 60 bar air pressure in the headspace of the reactor at room temperature, translated to the molar ratio of oxygen to feed) on the combined yield of FDCA+FDCA mono-methyl ester in the oxidation of MMF with 0.78 mol % and 0.10 mol % Co catalyst (relative to the feed), and Co/Mn/Br ratios of 1/5/5, 1/3/20 and 1/5/20. The feed concentration in all experiments was 3.7 wt/wt %, the temperature was 180° C. and the experiments lasted 1 hr. A pressure of 20 bar air corresponded to an oxygen to feed ratio of 2.69 mole/mole; a pressure of 40 bar corresponded to an $O_2$/feed ratio of 5.68 mole/mole; and a pressure of 60 bar corresponded with an $O_2$/feed ratio of 8.07 mole/mole. Under these conditions, the lowest air pressure (20 bar) gives 73-82% yields of FDCA+FDCA methyl ester. The higher pressures show lower yields. The 1/5/20 catalyst shows highest combined FDCA+FDCA methyl ester yields. The lowest combined yields were observed for the low Br catalyst (1/5/5). This low Br catalyst is also most affected by the pressure. The data of these experiments is also given in Table 3.

Table 3 further shows the selectivity to FDCA monomethyl ester (FDCA1/2R) for the MMF oxidations. Under these conditions, the higher pressures give higher FDCA methyl ester yields (and consequently lower FDCA yields) and the lower Br catalyst (1/5/5) shows highest methyl ester yields.

Table 3 also shows the results of experiments with a low catalyst loading (0.10 mol % Co). The pressure effect on the FDCA+FDCA methyl ester yield is different than what was observed for the higher catalyst concentration of FIG. 5.

Example 4

Example 4 shows the effect of reaction time (0.5, 0.75 and 1 hour) on the combined yield of FDCA+FDCA mono-methyl ester in the oxidation of MMF with 0.78 mol % Co catalyst (relative to the feed), 3.7 wt/wt % feed concentration at 180° C. and 60 bar air. The air pressure corresponded to an O2/feed ratio of 8.07 mole/mole. The catalyst composition was varied having Co/Mn/Br ratios of 1/5/5, 1/3/20 and 1/5/20. Under these conditions it was found that the reaction time has hardly any effect on the combined FDCA+FDCA methyl ester yields. The data of these experiments are given in Table 4.

Example 5

Example 5 shows the effect of temperature (160, 180, 200 and 220° C.) on the combined yield of FDCA+FDCA monomethyl ester in the oxidation of MMF with 0.78 mol % Co catalyst (relative to the feed), 3.7 wt/wt % feed concentration for 1 hr. and Co/Mn/Br ratios of 1/5/5, 1/3/20 and 1/5/20 at 20 bars and at 60 bars. Under these conditions, the highest combined yield of FDCA+FDCA methyl ester is observed at 180° C. The data of these experiments are given in Table 5.

Example 6

Example 6 shows the effect of feed concentration (3.7, 7.4 and 1'1.1 wt %) on the combined yield of FDCA+FDCA mono-methyl ester in the oxidation of MMF with 0.78 mol % Co catalyst (relative to the feed) at 180° C. and 20 bar for 1 hr. The catalyst composition was varied having Co/Mn/Br ratios of 1/5/5, 1/3/20 and 1/5/20. Under these conditions, the yields of FDCA+FDCA methyl ester decrease slightly with increasing feed concentration. The data of these experiments are given in Table 6.

Example 7

Example 7 shows the effect of feed concentration (3.7, 7.4 and 11.1 wt %) on the yield of the intermediate 5-formyl-furancarboxylic acid (FFCA) in the oxidation of MMF with 0.78 mol % Co catalyst (relative to the feed) at 180° C. and 20 bar for 1 hr. The catalyst composition was varied having Co/Mn/Br ratios of 1/5/5, 1/3/20 and 1/5/20. Under these conditions, the yield of FFCA is negligible at 3.7 wt % feed concentration but increases slightly with increasing feed concentration. FFCA is undesired as it acts as a chain stopper in polycondensation reactions. The data of these experiments are given in Table 7.

Example 8

Example 8 shows the effect of the Co/Mn ratio (0/1 (only Mn), 1/60, 1/40, 1/20, 1/15, 1/10, 1/8, 1/6, 1/4, 3/2, 2/3 and 4/1) on the combined yield of FDCA+FDCA mono-methyl ester in the oxidation of MMF with 4 mol % Co+Mn catalyst (relative to the feed) and a fixed Br/(Co+Mn) ratio of 0.7. In all experiments the feed concentration was 3.7 wt/wt %, the temperature was 180° C., the air pressure was 20 bar and lasted 1 hr. The air pressure corresponded with an $O_2$/feed ratio of 2.69 mole/mole. Under these conditions, it is obvious that Co is required to get relevant FDCA+FDCA methyl ester yields but that even very low amounts of Co (Co/Mn of 0.0167) result in desired product formation. The data of these experiments are given in Table 8.

Example 9

Example 9 shows the effect of the Mn/Co ratio (0/1 (only Co), 1/80, 1/60, 1/40, 1/20, 1/10, 1/4, 2/3, 3/2 and 4/1) on the combined yield of FDCA+FDCA mono-methyl ester in the oxidation of MMF with 4 mol % Co+Mn catalyst (relative to the feed) and a fixed Br/(Co+Mn) ratio of 0.7. In all experiments the feed concentration was 3.7 wt/wt %, the temperature was 180° C., the air pressure was 20 bar and lasted 1 hr. The air pressure corresponded with an $O_2$/feed ratio of 2.69 mole/mole. Under these conditions, it is obvious that also Mn is required to get relevant FDCA+FDCA methyl ester yields but that in this case, at the lowest amounts of Mn (Co/Mn<20/1) only low amounts of the desired products were observed. The highest FDCA+FDCA methyl ester yields were observed for Mn/Co 1/4. The data of these experiments are given in Table 9.

Example 10

Example 10 shows the effect of the Br amount (Br/(Co+Mn)=0.1, 0.25, 0.4, 0.5, 0.7 and 0.9) on the combined yield of FDCA+FDCA mono-methyl ester in the oxidation of MMF with 4 mol % Co+Mn catalyst (relative to the feed). In all experiments the feed concentration was 3.7 wt/wt %, the temperature was 180° C., the air pressure was 20 bar and lasted 1 hr. The air pressure corresponded with an $O_2$/feed ratio of 2.69 mole/mole. Under these conditions, it is obvious that the yield of FDCA+FDCA methyl ester increases from 57-63% at the lowest amount of Br (Br/Co+Mn)=0.1) to 71-77% at the highest amount of Br (Br/(Co+Mn)=0.9). The data of these experiments are given in Table 10.

TABLE 1

Example 1

| Experiment No. | Feed | Catalyst Composition Co/Mn/Br | Feed concentration [wt %] | Conversion [%] | s FDCA [%] | s FDCA1/2R [%] | s Furandicarboxylics [%] |
|---|---|---|---|---|---|---|---|
| 1a | EMF | 1/5/5 | 4 | 100 | 42.68 | 15.08 | 57.76 |
| 1b | MMF | 1/5/5 | 3.7 | 100 | 32.49 | 28.40 | 60.89 |
| 1c | EMF/HMF | 1/5/5 | 3.6 | 100 | 53.31 | 7.38 | 60.69 |
| 1d | MMF/HMF | 1/5/5 | 3.5 | 100 | 56.04 | 10.48 | 66.52 |
| 1e | EMF | 1/3/20 | 4 | 100 | 58.23 | 9.34 | 67.57 |
| 1f | MMF | 1/3/20 | 3.7 | 100 | 57.48 | 15.80 | 73.28 |
| 1g | EMF/HMF | 1/3/20 | 3.6 | 100 | 65.10 | 4.54 | 69.63 |
| 1h | MMF/HMF | 1/3/20 | 3.5 | 100 | 68.31 | 5.62 | 73.93 |
| 1i | EMF | 1/5/20 | 4 | 100 | 59.31 | 9.91 | 69.21 |
| 1j | MMF | 1/5/20 | 3.7 | 100 | 60.47 | 16.20 | 76.66 |
| 1k | EMF/HMF | 1/5/20 | 3.6 | 100 | 66.49 | 5.22 | 71.70 |
| 1l | MMF/HMF | 1/5/20 | 3.5 | 100 | 71.50 | 6.11 | 77.61 |

TABLE 2

Example 2

| Experiment No. | Feed | Catalyst concentration [Co mol %] | Catalyst Composition Co/Mn/Br | Conversion [%] | s FDCA [%] | s FDCA1/2R [%] | s Furandicarboxylics [%] |
|---|---|---|---|---|---|---|---|
| 2a | MMF | 0.10 | 1/5/5 | 100.00 | 13.99 | 10.86 | 24.84 |
| 2b | MMF | 0.10 | 1/3/20 | 100.00 | 15.50 | 10.60 | 26.11 |
| 2c | MMF | 0.10 | 1/5/20 | 100.00 | 18.90 | 12.10 | 31.00 |
| 2d | MMF | 0.78 | 1/5/5 | 100.00 | 31.42 | 28.38 | 59.80 |
| 2e | MMF | 0.78 | 1/3/20 | 100.00 | 58.13 | 15.42 | 73.54 |
| 2f | MMF | 0.78 | 1/5/20 | 100.00 | 60.77 | 16.17 | 76.94 |
| 2g | MMF | 1.56 | 1/5/5 | 100.00 | 46.01 | 26.90 | 72.91 |
| 2h | MMF | 1.56 | 1/3/20 | 100.00 | 68.07 | 9.60 | 77.67 |
| 2i | MMF | 1.56 | 1/5/20 | 100.00 | 67.89 | 9.82 | 77.71 |
| 2j | MMF | 1.95 | 1/5/5 | 100.00 | 51.93 | 24.93 | 76.86 |
| 2k | MMF | 1.95 | 1/3/20 | 100.00 | 67.29 | 8.91 | 76.21 |
| 2l | MMF | 1.95 | 1/5/20 | 100.00 | 66.10 | 9.10 | 75.20 |

TABLE 3

Example 3

| Experiment No. | Feed | Catalyst concentration [Co mol %] | Catalyst Composition Co/Mn/Br | $O_2$/Feed [mol/mol] | Conversion [%] | s FDCA [%] | s FDCA1/2R [%] | s Furandicarboxylics [%] |
|---|---|---|---|---|---|---|---|---|
| 3a | MMF | 0.78 | 1/5/5 | 2.69 | 100.00 | 54.98 | 19.07 | 74.05 |
| 3b | MMF | 0.78 | 1/3/20 | 2.69 | 100.00 | 69.83 | 8.57 | 78.40 |
| 3c | MMF | 0.78 | 1/5/20 | 2.69 | 100.00 | 72.20 | 10.07 | 82.27 |
| 3d | MMF | 0.78 | 1/5/5 | 5.68 | 100.00 | 41.17 | 26.98 | 68.15 |
| 3e | MMF | 0.78 | 1/3/20 | 5.68 | 100.00 | 64.13 | 11.93 | 76.06 |
| 3f | MMF | 0.78 | 1/5/20 | 5.68 | 100.00 | 67.07 | 12.36 | 79.43 |
| 3g | MMF | 0.78 | 1/5/5 | 8.07 | 100.00 | 31.42 | 28.38 | 59.80 |
| 3h | MMF | 0.78 | 1/3/20 | 8.07 | 100.00 | 58.13 | 15.42 | 73.54 |
| 3i | MMF | 0.78 | 1/5/20 | 8.07 | 100.00 | 60.77 | 16.17 | 76.94 |
| 3j | MMF | 0.10 | 1/5/5 | 2.69 | 100.00 | 4.66 | 6.83 | 11.49 |
| 3k | MMF | 0.10 | 1/3/20 | 2.69 | 100.00 | 8.88 | 13.33 | 22.21 |
| 3l | MMF | 0.10 | 1/5/20 | 2.69 | 100.00 | 8.27 | 8.18 | 16.44 |
| 3m | MMF | 0.10 | 1/5/5 | 5.68 | 100.00 | 15.22 | 13.07 | 28.29 |
| 3n | MMF | 0.10 | 1/3/20 | 5.68 | 100.00 | 16.66 | 12.56 | 29.22 |
| 3o | MMF | 0.10 | 1/5/20 | 5.68 | 100.00 | 21.66 | 13.01 | 34.67 |
| 3p | MMF | 0.10 | 1/5/5 | 8.07 | 100.00 | 13.99 | 10.86 | 24.84 |
| 3r | MMF | 0.10 | 1/3/20 | 8.07 | 100.00 | 15.50 | 10.60 | 26.11 |
| 3s | MMF | 0.10 | 1/5/20 | 8.07 | 100.00 | 26.76 | 17.63 | 44.38 |

TABLE 4

Example 4

| Experiment No. | Feed | Reaction time [Hours] | Catalyst Composition Co/Mn/Br | Conversion [%] | s FDCA [%] | s FDCA1/2R [%] | s Furandicarboxylics [%] |
|---|---|---|---|---|---|---|---|
| 4a | MMF | 1 | 1/5/5 | 100.00 | 31.42 | 28.38 | 59.80 |
| 4b | MMF | 1 | 1/3/20 | 100.00 | 58.13 | 15.42 | 73.54 |
| 4c | MMF | 1 | 1/5/20 | 100.00 | 60.77 | 16.17 | 76.94 |
| 4d | MMF | 0.75 | 1/5/5 | 100.00 | 35.03 | 28.83 | 63.86 |
| 4e | MMF | 0.75 | 1/3/20 | 100.00 | 59.66 | 14.66 | 74.32 |
| 4f | MMF | 0.75 | 1/5/20 | 100.00 | 64.98 | 14.09 | 79.07 |
| 4g | MMF | 0.5 | 1/5/5 | 100.00 | 31.51 | 29.57 | 61.08 |
| 4h | MMF | 0.5 | 1/3/20 | 100.00 | 58.15 | 15.57 | 73.71 |
| 4i | MMF | 0.5 | 1/5/20 | 100.00 | 62.16 | 15.73 | 77.89 |

TABLE 5

Example 5

| Experiment No. | Feed | Temperature [° C.] | Catalyst Composition Co/Mn/Br | $O_2$/Feed [mol/mol] | Conversion [%] | s FDCA [%] | s FDCA1/2R [%] | s Furandicarboxylics [%] |
|---|---|---|---|---|---|---|---|---|
| 5a | MMF | 180 | 1/5/5 | 8.07 | 100.00 | 31.42 | 28.38 | 59.80 |
| 5b | MMF | 180 | 1/5/20 | 8.07 | 100.00 | 60.77 | 16.17 | 76.94 |
| 5c | MMF | 180 | 1/3/20 | 8.07 | 100.00 | 58.13 | 15.42 | 73.54 |
| 5d | MMF | 200 | 1/5/5 | 8.07 | 100.00 | 40.07 | 21.37 | 61.44 |
| 5e | MMF | 200 | 1/5/20 | 8.07 | 100.00 | 58.35 | 9.20 | 67.55 |
| 5f | MMF | 200 | 1/3/20 | 8.07 | 100.00 | 59.10 | 8.49 | 67.58 |
| 5g | MMF | 220 | 1/5/5 | 8.07 | 100.00 | 41.24 | 11.39 | 52.63 |
| 5h | MMF | 220 | 1/5/20 | 8.07 | 100.00 | 47.08 | 2.97 | 50.05 |
| 5i | MMF | 220 | 1/3/20 | 8.07 | 100.00 | 43.76 | 3.03 | 46.79 |
| 5j | MMF | 160 | 1/5/5 | 8.07 | 100.00 | 27.37 | 27.39 | 54.76 |
| 5k | MMF | 160 | 1/5/20 | 8.07 | 100.00 | 55.57 | 15.19 | 70.76 |
| 5l | MMF | 160 | 1/3/20 | 8.07 | 100.00 | 53.54 | 14.52 | 68.07 |
| 5m | MMF | 180 | 1/5/5 | 2.69 | 100.00 | 54.98 | 19.07 | 74.05 |
| 5n | MMF | 180 | 1/5/20 | 2.69 | 100.00 | 69.83 | 8.57 | 78.40 |
| 5o | MMF | 180 | 1/3/20 | 2.69 | 100.00 | 72.20 | 10.07 | 82.27 |
| 5p | MMF | 200 | 1/5/5 | 2.69 | 100.00 | 58.10 | 12.47 | 70.57 |
| 5q | MMF | 200 | 1/5/20 | 2.69 | 100.00 | 70.01 | 6.29 | 76.29 |
| 5r | MMF | 200 | 1/3/20 | 2.69 | 100.00 | 69.82 | 5.28 | 75.11 |
| 5s | MMF | 220 | 1/5/5 | 2.69 | 100.00 | 59.24 | 9.31 | 68.55 |
| 5t | MMF | 220 | 1/5/20 | 2.69 | 100.00 | 70.50 | 2.82 | 73.32 |
| 5u | MMF | 220 | 1/3/20 | 2.69 | 100.00 | 68.61 | 2.51 | 71.12 |
| 5v | MMF | 160 | 1/5/5 | 2.69 | 100.00 | 48.47 | 21.69 | 70.16 |
| 5w | MMF | 160 | 1/5/20 | 2.69 | 100.00 | 66.85 | 10.40 | 77.25 |
| 5x | MMF | 160 | 1/3/20 | 2.69 | 100.00 | 65.73 | 9.80 | 75.53 |

TABLE 6

Example 6

| Experiment No. | Feed | Catalyst Composition Co/Mn/Br | Feed concentration [wt %] | Conversion [%] | s FDCA [%] | s FDCA1/2R [%] | s Furandicarboxylics [%] |
|---|---|---|---|---|---|---|---|
| 6a | MMF | 1/5/5 | 3.7 | 100.00 | 54.81 | 18.31 | 73.12 |
| 6b | MMF | 1/5/20 | 3.7 | 100.00 | 71.79 | 9.42 | 81.21 |
| 6c | MMF | 1/3/20 | 3.7 | 100.00 | 68.44 | 8.80 | 77.24 |
| 6d | MMF | 1/5/5 | 7.4 | 100.00 | 54.90 | 17.36 | 72.26 |
| 6e | MMF | 1/5/20 | 7.4 | 100.00 | 68.56 | 9.41 | 77.97 |
| 6f | MMF | 1/3/20 | 7.4 | 100.00 | 65.32 | 9.17 | 74.48 |
| 6g | MMF | 1/5/5 | 11.1 | 100.00 | 52.82 | 15.63 | 68.45 |
| 6h | MMF | 1/5/20 | 11.1 | 100.00 | 64.70 | 8.97 | 73.67 |
| 6i | MMF | 1/3/20 | 11.1 | 100.00 | 62.56 | 8.39 | 70.95 |

TABLE 7

Example 7

| Experiment No. | Feed | Catalyst Composition Co/Mn/Br | Feed concentration [wt %] | Conversion [%] | s FFCA [%] |
|---|---|---|---|---|---|
| 6a | MMF | 1/5/5 | 3.7 | 100.00 | 0.00 |
| 6b | MMF | 1/5/20 | 3.7 | 100.00 | 0.00 |
| 6c | MMF | 1/3/20 | 3.7 | 100.00 | 0.00 |
| 6d | MMF | 1/5/5 | 7.4 | 100.00 | 0.00 |
| 6e | MMF | 1/5/20 | 7.4 | 100.00 | 1.32 |
| 6f | MMF | 1/3/20 | 7.4 | 100.00 | 1.34 |
| 6g | MMF | 1/5/5 | 11.1 | 100.00 | 1.61 |
| 6h | MMF | 1/5/20 | 11.1 | 100.00 | 3.11 |
| 6i | MMF | 1/3/20 | 11.1 | 100.00 | 2.70 |

TABLE 8

Example 8

| Experiment No. | Feed | Catalyst concentration [(Co + Mn) mol %] | Co/Mn | Br/ (Co + Mn) | Conversion [%] | s FDCA [%] | s FDCA1/2R [%] | s Furandicarboxylics [%] |
|---|---|---|---|---|---|---|---|---|
| 8a | MMF | 4 | 0 | 0.7 | 100.00 | 1.69 | 5.71 | 7.40 |
| 8b | MMF | 4 | 0.0167 | 0.7 | 100.00 | 45.10 | 21.07 | 66.17 |
| 8c | MMF | 4 | 0.025 | 0.7 | 100.00 | 44.49 | 21.68 | 66.18 |
| 8d | MMF | 4 | 0.05 | 0.7 | 100.00 | 43.28 | 23.51 | 66.79 |
| 8e | MMF | 4 | 0.067 | 0.7 | 100.00 | 44.03 | 23.18 | 67.21 |
| 8f | MMF | 4 | 0.10 | 0.7 | 100.00 | 48.99 | 22.70 | 71.69 |
| 8g | MMF | 4 | 0.13 | 0.7 | 100.00 | 49.71 | 22.41 | 72.12 |
| 8h | MMF | 4 | 0.17 | 0.7 | 100.00 | 48.90 | 23.77 | 72.66 |
| 8i | MMF | 4 | 0.25 | 0.7 | 100.00 | 55.20 | 21.98 | 77.18 |
| 8j | MMF | 4 | 0.67 | 0.7 | 100.00 | 56.52 | 20.73 | 77.25 |
| 8k | MMF | 4 | 1.50 | 0.7 | 100.00 | 57.60 | 18.82 | 76.42 |
| 8l | MMF | 4 | 4.00 | 0.7 | 100.00 | 55.87 | 17.96 | 73.84 |

TABLE 9

Example 9

| Experiment No. | Feed | Catalyst concentration [(Co + Mn) mol %] | Mn/Co | Br/ (Co + Mn) | Conversion [%] | s FDCA [%] | s FDCA1/2R [%] | s Furandicarboxylics [%] |
|---|---|---|---|---|---|---|---|---|
| 9a | MMF | 4 | 0 | 0.7 | 100.00 | 0.00 | 0.60 | 0.60 |
| 9b | MMF | 4 | 0.0125 | 0.7 | 100.00 | 4.96 | 9.80 | 14.76 |
| 9c | MMF | 4 | 0.025 | 0.7 | 100.00 | 3.97 | 8.56 | 12.53 |
| 9d | MMF | 4 | 0.05 | 0.7 | 100.00 | 15.31 | 13.91 | 29.22 |
| 9e | MMF | 4 | 0.10 | 0.7 | 100.00 | 38.59 | 19.16 | 57.75 |
| 9f | MMF | 4 | 0.25 | 0.7 | 100.00 | 55.87 | 17.96 | 73.84 |
| 9g | MMF | 4 | 0.67 | 0.7 | 100.00 | 57.60 | 18.82 | 76.42 |
| 9h | MMF | 4 | 1.50 | 0.7 | 100.00 | 56.52 | 20.73 | 77.25 |
| 9i | MMF | 4 | 4.00 | 0.7 | 100.00 | 55.20 | 21.98 | 77.18 |
| 9j | MMF | 4 | 5.99 | 0.7 | 100.00 | 48.04 | 22.60 | 70.64 |
| 9k | MMF | 4 | 8.00 | 0.7 | 100.00 | 47.58 | 22.58 | 70.15 |
| 9l | MMF | 4 | 10.00 | 0.7 | 100.00 | 48.57 | 22.04 | 70.61 |

TABLE 10

Example 10

| Experiment No. | Feed | Catalyst concentration [(Co + Mn) mol %] | Co/Mn | Br/ (Co + Mn) | Conversion [%] | s FDCA [%] | s FDCA1/2R [%] | s Furandicarboxylics [%] |
|---|---|---|---|---|---|---|---|---|
| 10a | MMF | 4 | 0.25 | 0.9 | 100.00 | 52.20 | 23.88 | 76.08 |
| 10b | MMF | 4 | 0.25 | 0.7 | 100.00 | 48.23 | 24.69 | 72.91 |
| 10c | MMF | 4 | 0.25 | 0.5 | 100.00 | 46.76 | 24.34 | 71.10 |
| 10d | MMF | 4 | 0.25 | 0.4 | 100.00 | 43.62 | 22.34 | 65.96 |
| 10e | MMF | 4 | 0.25 | 0.25 | 100.00 | 42.83 | 22.68 | 65.52 |
| 10f | MMF | 4 | 0.25 | 0.1 | 100.00 | 41.76 | 20.69 | 62.45 |
| 10g | MMF | 4 | 4.00 | 0.9 | 100.00 | 52.43 | 18.92 | 71.35 |
| 10h | MMF | 4 | 4.00 | 0.7 | 100.00 | 50.69 | 19.53 | 70.21 |
| 10i | MMF | 4 | 4.00 | 0.5 | 100.00 | 47.29 | 21.10 | 68.39 |
| 10j | MMF | 4 | 4.00 | 0.4 | 100.00 | 41.96 | 18.93 | 60.89 |
| 10k | MMF | 4 | 4.00 | 0.25 | 100.00 | 40.91 | 19.11 | 60.02 |
| 10l | MMF | 4 | 4.00 | 0.1 | 100.00 | 39.10 | 18.30 | 57.39 |

The invention claimed is:

1. A method for the preparation of 2,5-furandicarboxylic acid and/or an alkyl ester of 2,5-furandicarboxylic acid comprising the step of contacting a feed comprising a starting material selected from 5-alkoxymethylfurfural, 2,5-di(alkoxymethyl)furan and a mixture thereof wherein the alkyl group is methyl or ethyl, with an oxidant in the presence of an oxidation catalyst.

2. The method according to claim 1, wherein the feed comprises 5-hydroxymethylfurfural as a further starting material.

3. The method according to claim 1, wherein the oxidation catalyst comprises at least one metal selected from the group consisting of Co and Mn.

4. The method according to claim 1, wherein the oxidation catalyst comprises a source of bromine.

5. The method according to claim 3, wherein the oxidation catalyst contains both Co and Mn.

6. The method according to claim 5, wherein the oxidation catalyst comprises at least one additional metal.

7. The method according to claim 6, wherein the additional metal is Zr, Ce or a mixture thereof.

8. The method according to claim 1, wherein the oxidant is selected from oxygen, air or other oxygen-containing gases.

9. The method according to claim 1, wherein the feed and the oxidant are contacted at a temperature between 60 and 220° C.

10. The method according to claim 1, wherein a solvent or solvent mixture is present.

11. A method for the preparation of a dialkylester of 2,5-furandicarboxylic acid, comprising preparing 2,5-furandicarboxylic acid or an alkyl ester of 2,5-furandicarboxylic acid in a method comprising the step of contacting a feed comprising a starting material selected from 5-alkoxymethylfurfural, 2,5-di(alkoxymethyl)furan and a mixture thereof, with an oxidant in the presence of an oxidation catalyst, to obtain a reaction product, and reacting the reaction product with a $C_1$-$C_5$ alkyl alcohol to obtain the dialkyl ester of 2,5-furandicarboxylic acid.

12. The method according to claim 11, wherein the $C_1$-$C_5$ alkylalcohol is methanol and the dialkyl ester is the dimethylester of 2,5-furan dicarboxylic acid.

13. The method according to claim 9, wherein the feed and the oxidant are contacted at a temperature, between 100 and 210° C.

14. The method according to claim 9, wherein the feed and the oxidant are contacted at a temperature between 150 and 200° C.

15. The method according to claim 9, wherein the feed and the oxidant are contacted at a temperature between 160 and 190° C.

16. The method according to claim 10, wherein the solvent contains a monocarboxylic acid functional group.

17. The method according to claim 10, wherein the solvent contains acetic acid or a mixture of acetic acid and water.

* * * * *